United States Patent
Nelson et al.

(10) Patent No.: US 6,177,564 B1
(45) Date of Patent: Jan. 23, 2001

(54) PROCESS FOR THE SYNTHESIS OF N-BENZYL-3-(4-FLUOROPHENYL)-1-4-OXAZIN-2-ONE

(75) Inventors: Todd D. Nelson, East Windsor; Mahadevan Bhupathy, Edison, both of NJ (US)

(73) Assignee: Merck & Co., Inc., Rahway, NJ (US)

( * ) Notice: Under 35 U.S.C. 154(b), the term of this patent shall be extended for 0 days.

(21) Appl. No.: 09/392,409

(22) Filed: Sep. 9, 1999

Related U.S. Application Data

(60) Provisional application No. 60/099,835, filed on Sep. 11, 1998.

(51) Int. Cl.[7] .................... C07D 265/30; A61K 31/5375
(52) U.S. Cl. .................... 544/106; 544/170; 544/175; 514/230.8; 514/231.2; 514/239.5
(58) Field of Search .............................. 514/231.2, 230.8, 514/239.5; 544/106, 175, 170

(56) References Cited

U.S. PATENT DOCUMENTS

| | | | |
|---|---|---|---|
| 5,668,280 | 9/1997 | Alabaster et al. | 544/173 |
| 5,719,147 | 2/1998 | Dorn et al. | 514/227.5 |
| 6,046,325 | 4/2000 | Ashwood et al. | 544/173 |

OTHER PUBLICATIONS

Julius B. Cohen; Practical Organic Chemistry),Macmillan & Co.,pp. 252–252 & pp. 392–393, Jan. 1949.*
Evans, et al., *J. Am. Chem. Soc.* 1990, 112, 4011–4030.
Chakraborty, et al., *J. Org. Chem.* 1992, 57, 5462–5469.
Chakraborty, et al., *Tetrahedron* vol. 51, No. 33, 9179–9190, 1995.
Chang, et al., *J. Chem. Soc. Perkin Trans.*, 1994, 3587–3593.
Inaba, et al., *Bull. Chem. Soc. Jpn.*, 65, 2359–2365, 1992.
Swain, et al., *J. Med. Chem.*, 1995, 38, 4793–4805.
Zhu, et al., *Tetrahedron Letters*, vol. 36, No. 39, 7081–7084, 1995.

* cited by examiner

*Primary Examiner*—Mukund J. Shah
*Assistant Examiner*—Sudhaker Patel
(74) *Attorney, Agent, or Firm*—J. Eric Thies; David L. Rose

(57) ABSTRACT

The present invention is concerned with a novel process for the preparation of N-benzyl-3-(4-fluorophenyl)-1,4-oxazin-2-one of the formula:

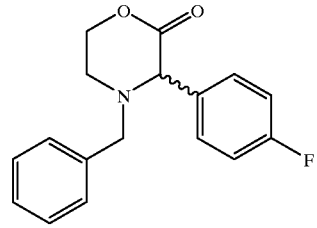

This compound is useful as an intermediate in the synthesis of compounds which possess pharmacological activity, in particular, as substance P (neurokinin-1) receptor antagonists.

23 Claims, No Drawings

PROCESS FOR THE SYNTHESIS OF N-BENZYL-3-(4-FLUOROPHENYL)-1-4-OXAZIN-2-ONE

This application claims the benefit of U.S. Provisional Application No. 60/099,835, filed Sep. 11, 1998.

BACKGROUND OF THE INVENTION

The present invention relates to processes for the preparation of a 1,4-oxazin-2-one derivative which is useful as an intermediate in the preparation of certain therapeutic agents. In particular, the present invention provides a process for the preparation of N-benzyl-3-(4-fluoro-phenyl)-1,4-oxazin-2-one which is an intermediate in the preparation of pharmaceutical compounds which are substance P (neurokinin-1) receptor antagonists.

U.S. Pat. No. 5,719,147 describes the preparation of benzyloxazinones by a two-step process starting from an optically pure glycine derivatives. Control of process parameters (e.g. reaction time, temperature, moisture content) is necessary to prevent racemisation in these steps. With reference to Example 59 in U.S. Pat. No. 5,719,147, N-benzyl-3-(S)-(4-fluorophenyl)-1,4-oxazin-2-one [3-(S)-(4-fluorophenyl)-4-benzyl-2-morpholinone] is prepared in several steps as follows:

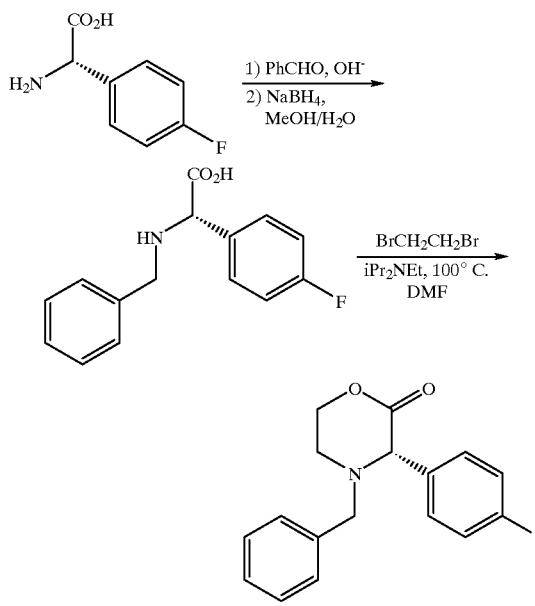

The optically pure (S)-(4-fluorophenyl)glycine is disclosed as having been prepared by means of a four-step asymmetric synthesis process which is based upon the procedure for the asymmetric synthesis of α-amino acids described by D. A. Evans et al., *J. Am. Chem. Soc.,* (1990) 112, 4011–4030. The complexity of this four-step process combined with the sensitive nature of the protection and double alkylation reactions to give the desired 1,4-oxazin-2-one, renders these prior art syntheses impracticable when attempted on anything other than a laboratory scale.

U.S. Pat. No. 5,668,280 describes an alternative procedure which utilizes racemic N-benzyl-3-(4-fluorophenyl)-1,4-oxazin-2-one as starting material and in a minimum of steps afforded product of high enantiomeric purity in high yield. Resolution of racemic N-benzyl-3-(4-fluorophenyl)-1,4-oxazin-2-one was achieved using (−)-3-bromocamphor-8-sulphonic acid (also referred to as (−)-3-BCS) in the presence of a racemising agent. While this is an effective method for obtaining substantially pure N-benzyl-3-(S)-(4-fluorophenyl)-1,4-oxazin-2-one, the use of (−)-3-BCS on a large scale is expensive. Furthermore, large quantities of (−)-3-BCS are not readily available.

It will be appreciated that chiral 3-(4-fluorophenyl)-1,4-oxazin-2-one derivatives are important intermediates for a particularly useful class of therapeutic agents. As such, there is a need for the development of a process for the preparation of N-benzyl-3-(4-fluoro-phenyl)-1,4-oxazin-2-one which is readily amenable to scale-up, uses cost-effective and readily available reagents and which is therefore capable of practical application to large scale manufacture.

General processes and intermediates have been disclosed in the art for the preparation of 5-substituted oxazinones (see *J. Chem. Soc. Perkin Trans.,* 1, 3587 (1994); *Tetrahedron,* 51, 9179 (1995); *Tetrahedron Lett.,* 36, 7081 (1995); *Bull. Chem. Soc. Jpn.,* 65, 2359 (1992); *J. Org. Chem.,* 57, 5462 (1992); *Tetrahedron Lett.,* 37, 4001 (1996)). The oxazinones prepared by these published methods have substitution at the 5-position of the oxazinone ring. In contrast to the previously known processes, the present invention provides effective methodology for the preparation of oxazinones which are unsubstituted at the 5-position of the oxazinone ring.

Accordingly, the subject invention provides a process for the preparation of N-benzyl-3(4-fluoro-phenyl)-1,4-oxazin-2-one via a very simple, short and highly efficient synthesis.

SUMMARY OF THE INVENTION

The novel process of this invention involves the synthesis of N-benzyl-3(4-fluorophenyl)-1,4-oxazin-2-one, and the useful intermediates obtained therein. In particular, the present invention is concerned with novel processes for the preparation of a compound of the formula:

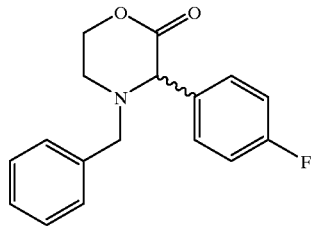

This compound is an intermediate in the synthesis of compounds which possess pharmacological activity. In particular, such compounds are substance P (neurokinin-1) receptor antagonists which are useful e.g., in the treatment of inflammatory diseases, psychiatric disorders, and emesis.

DETAILED DESCRIPTION OF THE INVENTION

The present invention is directed to processes for the preparation of N-benzyl-3-(4-fluoro-phenyl)-1,4-oxazin-2-one of the formula:

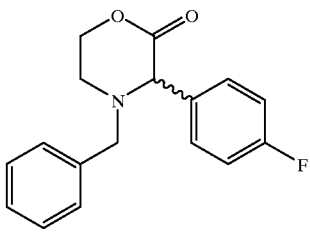

The general process for the preparation of N-benzyl-3-(4-fluorophenyl)-1,4-oxazin-2-one is as follows:

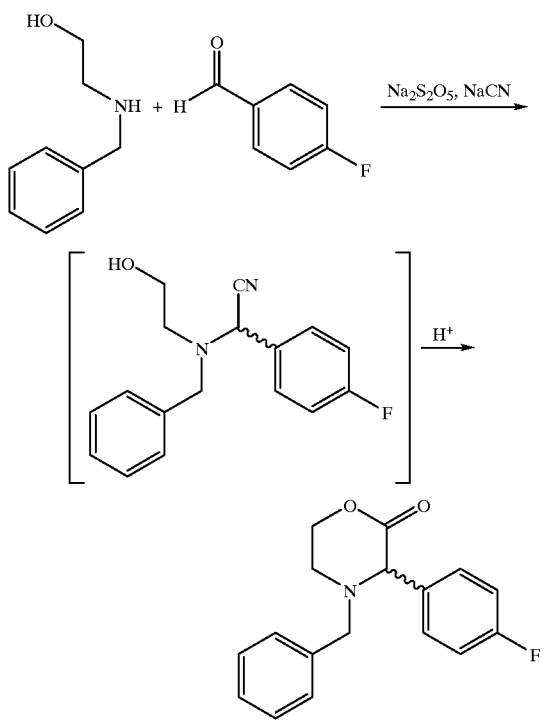

An embodiment of the present invention concerns a process for the preparation of a compound of the structural formula 4:

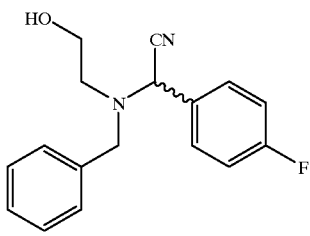

which comprises:

a) treating 4-fluorobenzaldehyde of the structural formula 1:

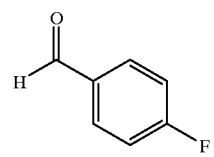

with sodium metabisulfite in a solvent followed by reaction with sodium cyanide or potassium cyanide to give 1-cyano-1-(4-fluorophenyl)methanol of the structural formula 2:

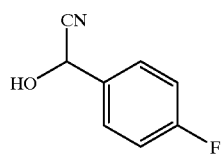

b) followed by treating the compound of the structural formula 2 with N-benzylethanolamine of the structural formula 3:

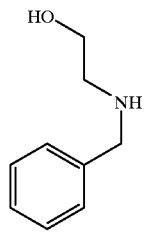

to give the compound of structural formula 4.

Although numerous cyanide sources may be employed in this process, sodium cyanide and potassium cyanide are preferred, and sodium cyanide is most preferred. This process may be carried out in a solvent such as an alcohol, such as methanol, ethanol, isopropanol, n-propanol or water, or a mixture thereof. The preferred solvent system is methanol/water or isopropanol/water, and the most preferred solvent is methanol/water. The preferred temperature range for the reaction of 4-fluorobenzaldehyde with sodium metabisulfite and sodium cyanide is between about 10 and about 50° C., a more prefered reaction temperature range is between about 20 and about 40° C., and the most preferred temperature is about 30° C. The preferred temperature range for the reaction of the compound of structural formula 2 with N-benzylethanolamine is between about 10 and about 50° C., a more prefered reaction temperature range is between about 20 and about 40° C., and the most preferred temperature range is about 30±2° C.

In the interest of efficiency, it is preferred that this reaction be conducted in situ without isolation of the compound of structural formula 4 following its preparation by the aforementioned process.

Another embodiment within the present invention concerns a process for the preparation of N-benzyl-3-(4-fluorophenyl)-1,4-oxazin-2-one of the structural formula 5:

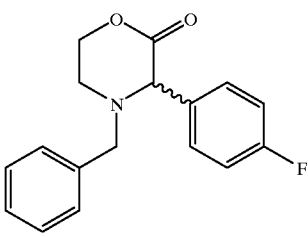

which comprises:
treating the compound of the structural formula 4:

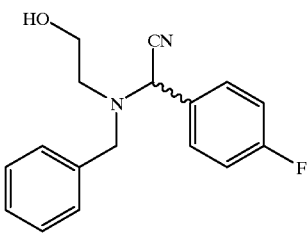

with a strong acid in a solvent. Optionally the free base of N-benzyl-3-(4-fluoro-phenyl)-1,4-oxazin-2-one may be formed by neutralization with a base.

Appropriate strong acids include: hydrochloric acid, including hydrogen chloride gas; methanesulfonic acid; trifluoroacetic acid; hydrogen bromide; hydrogen iodide; trifluoromethane-sulfonic acid; camphorsulfonic acid; sulfuric acid; phosphoric acid; and an arylsulfonic acid, such as benzenesulfonic acid, p-toluenesulfonic acid, and p-chlorobenzene-sulfonic acid. Preferred strong acids include: hydrochloric acid, including hydrogen chloride gas; methanesulfonic acid; trifluoroacetic acid; camphorsulfonic acid; benzenesulfonic acid, p-toluenesulfonic acid; and p-chlorobenzene-sulfonic acid. The most preferred strong acid is hydrochloric acid, including hydrogen chloride gas, and the most preferred strong acid is hydrogen chloride gas.

This process may be carried out in a suitable solvent such as an ether, for example, dioxane, or an ester, for example, ethyl acetate, isopropyl acetate, n-propyl acetate, isobutyl acetate, n-butyl acetate, sec-butyl acetate, n-butyl propionate, isobutyl propionate, ethyl butyrate, or n-propyl butyrate, water, or a mixture thereof. Dioxane, isopropyl acetate, isobutyl acetate, or isopropyl acetate/water are particularly preferred and isopropyl acetate/water is especially preferred. The preferred temperature range for the reaction is between about −10 and 50° C., a more prefered reaction temperature range is between about 30 and 45° C., and the most preferred temperature range is about 38±3° C. If desired, the free base may be formed by employing a weak base such as potassium bicarbonate, sodium bicarbonate, potassium carbonate or sodium carbonate.

In the interest of efficiency, it is preferred that this reaction be conducted in situ without isolation of the hydroxynitrile following its preparation by the aforementioned process.

A preferred processes within the general process for the preparation of N-benzyl-3-(4-fluorophenyl)-1,4-oxazin-2-one may be summarized as follows:

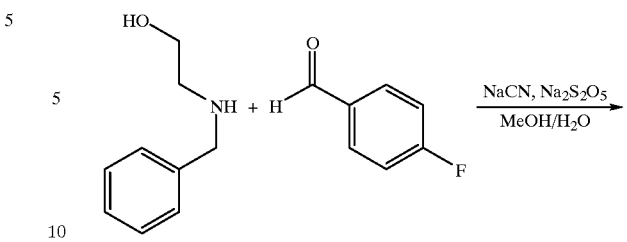

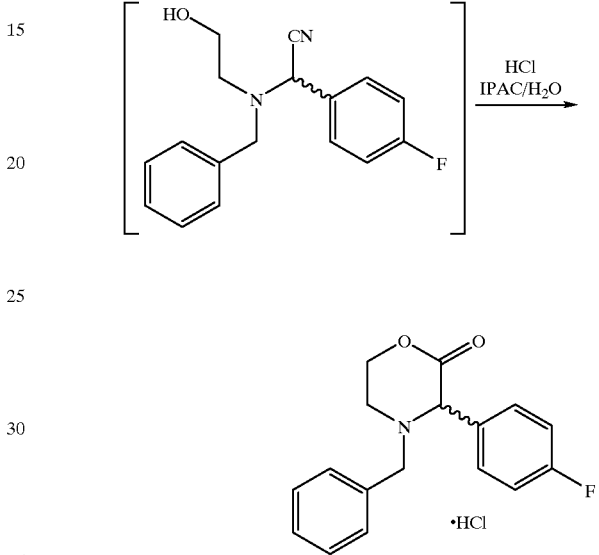

Many of the starting materials are either commercially available or known in the literature and others can be prepared following literature methods described for analogous compounds. The skills required in carrying out the reaction and purification of the resulting reaction products are known to those in the art. Purification procedures include crystallization, normal phase or reverse phase chromatography.

The following examples are provided for the purpose of further illustration only and are not intended to be limitations on the disclosed invention.

EXAMPLE 1

N-Benzyl-3-(4-fluorophenyl)-1,4-oxazin-2-one (Process A)

Sodium metabisulfite (5.70 g, 30 mmoles) was added to degassed water (47.5 mL), and the solid allowed to dissolve. 4-Fluoro-benzaldehyde (6.94 g, 55.9 mmoles) was added at ambient temperature, followed by methanol (2 mL), and the resultant mixture stirred for 30 minutes (internal temperature rises to 30° C. and a precipitate of the bisulfite addition complex forms within 5 minutes). Sodium cyanide (2.77 g, 56.5 mmoles) was added (temperature rises from 26 to 30° C.) and the mixture was stirred vigorously for 45 minutes.

N-Benzylethanolamine (8.84 g, 58.4 mmoles assuming 100% pure) was added, followed by methanol (12 mL), and the resultant mixture stirred vigorously for 5 hours at 30° C. and then overnight at ambient temperature to complete the reaction. Water (22.5 mL) and isopropyl acetate (59 mL) are added and the phases are separated. The organic layer was washed with water (3×22.5 mL) and then diluted to 100 mL by addition of isopropyl acetate. The water content was determined by Karl-Fisher at this level of dilution. The desired total water content was 1.108 g, 61.5 mmoles (1.1 equivalents w.r.t. 4-fluorobenzaldehyde). Assuming that the water content was above this limit (typical=1700 μg/100 μL), the solution is dried to below the desired water content by azeotropic distillation in vacuo at 40, add the appropriate volume of fresh isopropyl acetate, and then add water as necessary to reach the required specification. This should give a solution of the hydroxy-nitrile intermediate in isopropyl acetate (volume=100 mL, KF=1108 μg/100 μL). Hydrogen chloride gas (5.1 g, 140 mmoles) was bubbled into the stirred hydroxy-nitrile solution at room temperature (the temperature will rise to 40° C.) and the resultant slurry aged at 40° C. for 3–4 hours until no hydroxy-nitrile intermediate remains in the liquors.

To obtain the free-base, the slurry of the oxazinone HCl salt was added, with a 10 mL isopropyl acetate rinse, to a saturated aqueous solution of potassium bicarbonate (60 mL) [caution, frothing] and after stirring for 5 minutes the layers were separated. To the organic layer was added water (10 mL) and solid sodium metabisulfite (3 g), and after stirring for 5 minutes the layers were separated. The organic layer was then washed with water (10 mL). The organic layer was dried by azeotropic distillation under reduced pressure and diluted with isopropyl acetate to a final volume of 72 mL (Karl-Fisher<140 μg/ml). The solution assayed for 13.1 g oxazinone free base.

A 100 L round-bottomed flask was equipped with a thermocouple, overhead stirrer, $N_2$ inlet and an outlet to a cyanide scrubber (NaOH/bleach, pH≧12). The vessel was then charged with water (20.5 L) and sodium metabisulfite (2.46 kg). Upon complete dissolution, 4-fluorobenzaldehyde (3.00 kg) was added followed by a methanol (860 mL) rinse. After stirring vigorously for 35 min, sodium cyanide (1.197 kg) was added via a powder funnel to the white suspension. The powder funnel was rinsed with water (300 mL). [Cyanide halts cellular respiration and must be handled with extreme care. Persons involved in this reaction should have the appropriate training, wear the appropriate protective gear, and the antidote (amyl nitrite) should be positioned nearby (but not at the hood).]

The reaction mixture was vigorously stirred for 40 min and then N-benzylethanolamine (4.02 kg) was added followed by a MeOH (5.2 L) rinse. The two phase system was vigorously stirred at 30+2° C. for 5 h and then aged at room temperature for 8–16 hrs. To the reaction mixture was added water (9.7 L) and isopropyl acetate (25.5 L). After stirring vigorously for 15 min, the two phase system was transferred to a 100 L extractor for separation. The reaction vessel was rinsed with isopropyl acetate 2 L). After the removal of the aqueous layer, the organic layer was washed successively with water (9.7 L) and 20% sodium chloride (9.7 L). The organic layer was then diluted with isopropyl acetate (8 L). The final volume of the 2-[N-Benzyl-(2-hydroxyethyl)]-amino-4'-fluorophenyl-acetonitrile solution was ca. 40 L. Typically observe Karl-Fisher=13 mg/mL (520 g, 28.9 mol, 1,2 eq water). This solution of 2-[N-Benzyl-(2-hydroxyethyl)]-amino-4'-fluorophenyl-acetonitrile in isopropyl acetate was used directly in the next step.

EXAMPLE 2

N-Benzyl-3-(4-fluorophenyl)-1,4-oxazin-2-one (Process B)

Step 1: 2-[N-Benzyl-(2-hydroxyethyl)]-amino-4'-fluorophenyl-acetonitrile

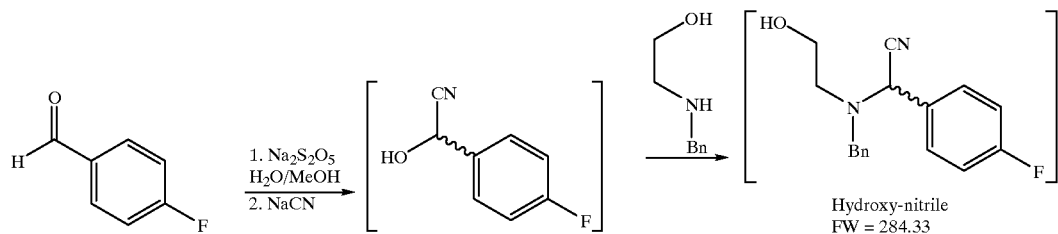

| Materials | FW | Amt | mol | eq |
| --- | --- | --- | --- | --- |
| Sodium metabisulfite | 190.10 | 2.46 kg | 12.9 | 0.54 |
| 4-Fluorobenzaldehyde (99.8%) | 124.11 | 3.00 kg | 24.1 | 1.00 |
| Sodium cyanide (97%) | 49.01 | 1.197 kg | 23.7 | 0.98 |
| N-benzylethanolamine (95%) | 151.21 | 4.02 kg | 25.3 | 1.05 |
| Water | 18.01 | 49.9 L | | |
| Methanol | d = 0.813 | 6.1 L | | |
| Isopropyl acetate | d = 0.872 | 35.5 L | | |
| Brine (20 wt %) | | 9.7 L | | |

Step 2: N-Benzyl-3-(4-fluorophenyl)-1,4-oxazine-2-one

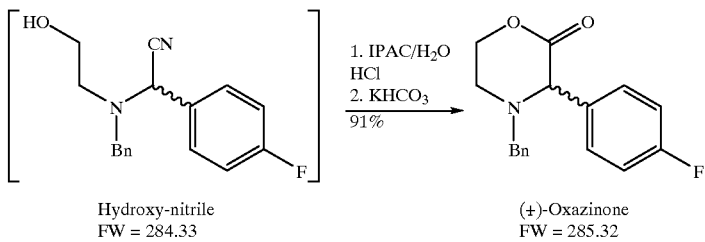

Hydroxy-nitrile
FW = 284.33

(±)-Oxazinone
FW = 285.32

| Materials | FW | Amt | mol | eq |
|---|---|---|---|---|
| Hydroxynitrile in isopropyl acetate | | 40 L | <23.7 | |
| Hydrogen chloride gas | 36.46 | 2.25 kg | 61.7 | 2.6 |
| Potassium bicarbonate | 100.12 | 5.5 kg | 54.9 | 2.3 |
| Sodium metabisulfite | 190.10 | 1.3 kg | 6.8 | |
| Water | | 33.6 L | | |
| Isopropyl acetate | d = 0.872 | 50 L | | |

A 100 L round-bottomed flask was equipped with an overhead stirrer, a subsurface hydrogen chloride gas inlet and a cyanide scrubber (NaOH/bleach, pH>12). The isopropyl acetate solution of 2-[N-Benzyl-(2-hydroxyethyl)]-amino-4'-fluorophenyl-acetonitrile from the previous step was charged into the reaction vessel and then cooled to 3±2° C. Hydrogen chloride gas (2.25 kg) was bubbled through the subsurface line to the stirred batch with the internal temperature being maintained at ≦40° C. After complete addition, the reaction mixture was aged at 38±2° C. for 1 h and then gradually cooled to room temperature. Typically, the reaction is complete in 6 h at 38±3° C. The reaction mixture can be aged overnight at room temperature for convenience.

The slurry was transferred at room temperature to a filtered solution of 5.5 kg of potassium bicarbonate in 25 L of water in a 100 L batch extractor. The original reaction vessel was rinsed with isopropyl acetate (8 L) and this was also transferred to the potassium bicarbonate solution. The resulting two phase system was stirred at room temperature until complete dissolution of the (±)-oxazinone hydrochloride salt (<30 min) occurred. $CO_2$ release occurs upon bicarbonate quench. Typical final pH =7.3: if the solution is not basic, additional potassium bicarbonate solution is added.

The two-phase system was allowed to settle for 10 min and then separated. The organic layer was assayed (HPLC) for 4-fluorobenzaldehyde and the aqueous layer was assayed for cyanide content. Typically, <3 LCAP 4-fluorobenzaldehyde (HPLC conditions below) and <200 ppm cyanide is observed.

HPLC Conditions:
Column: Zorbax RX-C8, 4.6×250 mm, 5 μm particle size
Mobile Phase: A) acetonitrile—B) 0.1% $H_3PO_4$ buffered water
Step gradient: 20:80 A:B to 80:20 A:B over 15 min, hold for 5 min, 80:20 A:B to 20:80 A:B over 5 min., Flow Rate: 1.0 mL/min, @45.0° C., Detection @220 nm
4-Fluorobenzaldehyde: Rt=10.5 min, Hydroxynitrile: Rt=15.0 min, Oxazinone: Rt=15.8 min The organic layer was then charged with a solution of 1.3 kg of sodium metabisulfite in 4.3 L of water and stirred for 25 min. The 4-fluorobenzaldehyde content in the organic phase (before separation) was assayed by HPLC. If the relative area % of 4-fluorobenzaldehyde (to oxazinone) is >0.6 %, the reaction mixture is stirred an additional 15 min, reassayed and repeated until the above criteria is met.

The two layers were separated and the organic portion was washed with water (4.3 L). The batch was filtered (5μ in-line filter) and diluted with isopropyl acetate (12 L). This was concentrated under vacuum (26 in), diluted with isopropyl acetate (12 L), re-concentrated to a final volume of 38 L, diluted with isopropyl acetate (18 L) and re-concentrated to a final batch volume of 44 L. If the Karl-Fisher was >300 microgram/mL, the distillation was continued with additional isopropyl acetate and the final batch volume is adjusted to 44 L with isopropyl acetate. A solution of (±)-N-Benzyl-3-(4-fluoro-phenyl)-1,4-oxazine-2-one free base (140 g/L, 91%) was obtained.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of the structural formula 5:

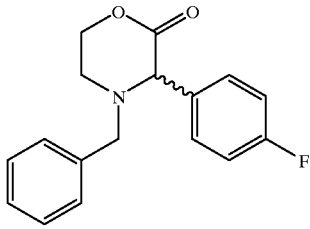

5 which comprises:
a) treating 4-fluorobenzaldehyde of the structural formula 1:

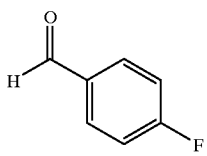

1 with sodium metabisulfite in a first solvent followed by reaction with a cyanide source selected from: sodium cyanide and potassium cyanide, and the reaction is conducted at a temperature range of about 10 to about 50 degree Celsius, to give 1-cyano-1-(4-fluorophenyl) methanol of the structural formula 2:

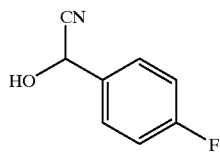

2 b) followed by treating the compound of the structural formula 2 with N-benzylethanolamine of the structural formula 3:

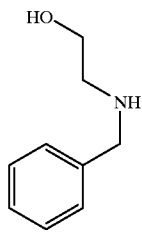

3 is reacted at a temperature range of about 10 to about 50 degree Celsius to give the compound of structural formula 4:

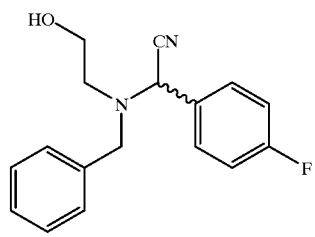

4 c) followed by treating the compound of the structural formula 4 with a strong acid in a second solvent to give the compound of structural formula 5.

2. The process of claim 1 wherein the cyanide source is sodium cyanide.

3. The process of claim 1 wherein the first solvent is selected from: methanol; ethanol; isopropanol; n-propanol; water; and mixtures thereof.

4. The process of claim 1 wherein the first solvent is selected from: methanol/water and isopropanol/water.

5. The process of claim 1 wherein the first solvent is methanol/water.

6. The process of claim 1 wherein the reaction of 4-fluorobenzaldehyde with sodium metabisulfite and sodium cyanide is conducted at a temperature of about 30° C.

7. The process of claim 1 wherein the reaction of the compound of structural formula 2 with N-benzyl-ethanolamine is conducted at a temperature of about 30±2° C.

8. The process of claim 1 wherein the strong acid is selected from: hydrochloric acid, including hydrogen chloride gas; methanesulfonic acid; trifluoroacetic acid; hydrogen bromide; hydrogen iodide; trifluoromethane-sulfonic acid; camphorsulfonic acid; sulfuric acid; phosphoric acid; benzenesulfonic acid, p-toluenesulfonic acid, and p-chlorobenzene-sulfonic acid.

9. The process of claim 1 wherein the strong acid is selected from: hydrochloric acid, including hydrogen chloride gas; methanesulfonic acid; trifluoroacetic acid; camphorsulfonic acid; benzenesulfonic acid, p-toluenesulfonic acid; and p-chlorobenzene-sulfonic acid.

10. The process of claim 1 wherein the strong acid is hydrochloric acid, including hydrogen chloride gas.

11. The process of claim 1 wherein the strong acid is hydrogen chloride gas.

12. The process of claim 1 wherein the second solvent is selected from: ethyl acetate; isopropyl acetate; n-propyl acetate; isobutyl acetate; n-butyl acetate; sec-butyl acetate; n-butyl propionate; isobutyl propionate; ethyl butyrate; or n-propyl butyrate; dioxane; water; and mixtures thereof.

13. The process of claim 1 wherein the second solvent is isopropyl acetate/water.

14. A process for the preparation of a compound of the structural formula 4:

which comprises:
 a) treating 4-fluorobenzaldehyde of the structural formula 1:

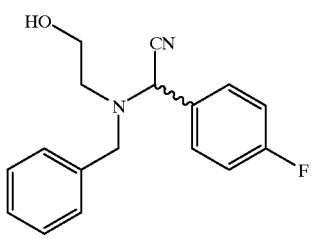

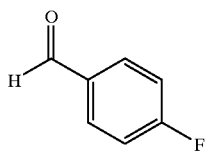

with sodium metabisulfite in a solvent followed by reaction with a cyanide source selected from: sodium cyanide and potassium cyanide, to give 1-cyano-1-(4-fluorophenyl)methanol of the structural formula 2:

b) followed by treating the compound of the structural formula 2 with N-benzylethanolamine of the structural formula 3:

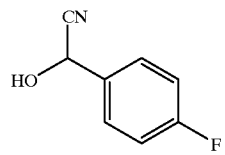

to give the compound of structural formula 4.

15. The process of claim 14 wherein the cyanide source is sodium cyanide.

16. The process of claim 14 wherein the solvent is selected from: methanol; ethanol; isopropanol; n-propanol; water; and mixtures thereof.

17. The process of claim 14 wherein the solvent is methanol/water.

18. A process for the preparation of a compound of the structural formula 5:

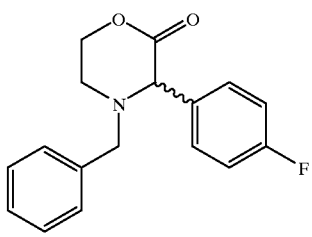

which comprises:
 treating the compound of the structural formula 4:

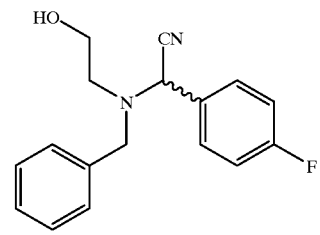

with a strong acid in a solvent to give the compound of structural formula 5.

19. The process of claim 18 wherein the strong acid is selected from: hydrochloric acid, including hydrogen chloride gas; methanesulfonic acid; trifluoroacetic acid; hydrogen bromide; hydrogen iodide; trifluoromethane-sulfonic acid; camphorsulfonic acid; sulfuric acid; phosphoric acid; benzenesulfonic acid, p-toluenesulfonic acid, and p-chlorobenzene-sulfonic acid.

20. The process of claim 18 wherein the strong acid is selected from: hydrochloric acid, including hydrogen chloride gas; methanesulfonic acid; trifluoroacetic acid; camphorsulfonic acid; benzesulfonic acid, p-toluenesulfonic acid; and p-chlorobenzene-sulfonic acid.

21. The process of claim 18 wherein the strong acid is hydrogen chloride gas.

22. The process of claim 18 wherein the solvent is selected from: ethyl acetate; isopropyl acetate; n-propyl acetate; isobutyl acetate; n-butyl acetate; sec-butyl acetate; n-butyl propionate; isobutyl propionate; ethyl butyrate; or n-propyl butyrate; dioxane; water; and mixtures thereof.

23. The process of claim 18 wherein the solvent is isopropyl acetate/water.

* * * * *